(12) United States Patent
Furuya et al.

(10) Patent No.: US 9,133,112 B2
(45) Date of Patent: Sep. 15, 2015

(54) PROCESS FOR PREPARING β-MERCAPTOCARBOXYLIC ACID

(71) Applicant: Mitsui Chemicals, Inc., Minato-ku (JP)

(72) Inventors: Masayuki Furuya, Arao (JP); Tatsuya Ogawa, Ravenna (IT); Takeshi Nishimura, Yanagawa (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/359,439

(22) PCT Filed: Nov. 20, 2012

(86) PCT No.: PCT/JP2012/007452
§ 371 (c)(1),
(2) Date: May 20, 2014

(87) PCT Pub. No.: WO2013/076969
PCT Pub. Date: May 30, 2013

(65) Prior Publication Data
US 2014/0323761 A1 Oct. 30, 2014

(30) Foreign Application Priority Data

Nov. 21, 2011 (JP) ................................. 2011-253455

(51) Int. Cl.
*C07C 319/04* (2006.01)
*C07C 319/24* (2006.01)
*C07C 319/28* (2006.01)

(52) U.S. Cl.
CPC ............ *C07C 319/04* (2013.01); *C07C 319/24* (2013.01); *C07C 319/28* (2013.01)

(58) Field of Classification Search
CPC .... C07C 319/04; C07C 319/24; C07C 319/28
USPC ........................................................ 562/606
See application file for complete search history.

(56) References Cited

U.S. PATENT DOCUMENTS

| 3,948,816 A | 4/1976 | Helmlinger et al. |
| 4,067,901 A | 1/1978 | Gladstone et al. |
| 5,157,147 A | 10/1992 | Chisholm et al. |
| 5,256,818 A | 10/1993 | Tomioka |
| 6,689,907 B1 | 2/2004 | Labat |

FOREIGN PATENT DOCUMENTS

| GB | 1336037 A | 11/1973 |
| JP | 40-15170 B1 | 7/1965 |
| JP | 47-12317 A | 6/1972 |
| JP | 52-36623 A | 3/1977 |
| JP | 58-54138 B2 | 12/1983 |
| JP | 59-29655 | 2/1984 |

(Continued)

OTHER PUBLICATIONS

International Search Report (PCT/ISA/210) mailed on Feb. 26, 2013, by the Japanese Patent Office as the International Searching Authority for International Application No. PCT/JP2012/007452.
International Search Report (PCT/ISA/210) mailed on Feb. 26, 2013, by the Japanese Patent Office as the International Searching Authority for International Application No. PCT/JP2012/007451.
Office Action issued in corresponding Japanese application on Sep. 24, 2014.
Office Action issued in corresponding Japanese application on Jan. 20, 2015 (3 pages).

(Continued)

*Primary Examiner* — Shailendra Kumar
(74) *Attorney, Agent, or Firm* — Buchanan, Ingersoll & Rooney PC

(57) ABSTRACT

A process for preparing β-mercaptocarboxylic acid is provided with Step a for reacting a compound represented by a formula: $X^1{}_2S$ or a compound represented by a formula: $X^2SH$, alkali hydroxide represented by a formula: $X^3OH$ (the X groups being defined), and unsaturated carboxylic acid represented by the following General Formula (1) to obtain a reaction solution including a compound represented by the following General Formula (2) and a compound represented by the following General Formula (3), Step b for neutralizing the reaction solution obtained in Step a with an acid to obtain a reaction solution including β-mercaptocarboxylic acid represented by the following General Formula (4) and a compound represented by the following General Formula (5), Step c for distillation-refining the reaction solution obtained in Step b to obtain the β-mercaptocarboxylic acid, and Step d for returning a distillation residue in Step c to Step a.

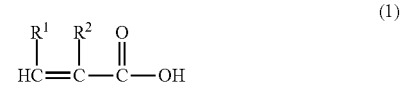

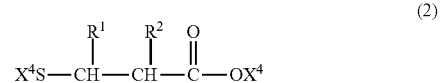

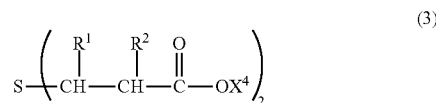

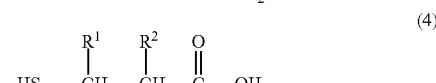

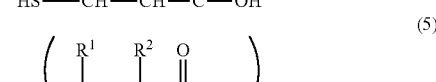

6 Claims, No Drawings

(56) References Cited

FOREIGN PATENT DOCUMENTS

| | | |
|---|---|---|
| JP | 61-254555 A | 11/1986 |
| JP | 2-121962 A | 5/1990 |
| JP | 4-9363 A | 1/1992 |
| JP | 4-273851 A | 9/1992 |
| JP | 09-249639 A | 9/1997 |
| JP | 10-95760 | 4/1998 |
| JP | 2000-501723 A | 2/2000 |
| JP | 2001-187778 A | 7/2001 |
| WO | WO 2010/095745 A1 | 8/2010 |

OTHER PUBLICATIONS

Office Action issued in corresponding Chinese application on Jan. 4, 2015 (5 pages).

PROCESS FOR PREPARING β-MERCAPTOCARBOXYLIC ACID

This application is a 371 of PCT/JP2012/007452, filed Nov. 20, 2012.

TECHNICAL FIELD

The present invention relates to a process for preparing β-mercaptocarboxylic acid.

BACKGROUND ART

β-mercaptocarboxylic acid is a compound which is useful as a raw material for organic synthesis products including agricultural chemicals, and pharmaceuticals, and is useful as a raw material for a stabilizer of vinyl chloride, a cross-linking agent of an epoxy resin and an acrylic acid ester polymer, and a plastic lens monomer.

Examples of the process for preparing β-mercaptocarboxylic acid are as follows.

Patent Document 1 discloses a method in which acrylic acid and thiosulfate are reacted in an aqueous medium, as a result to produce Bunte salt as a precursor of β-mercaptopropionic acid, and then, the Bunte salt is hydrolyzed in the presence of an acid.

Patent Document 2 discloses a method in which an acrylic acid alkali salt aqueous solution is added to an aqueous solution of alkali hydrosulfide to react in the presence of an alkali hydroxide, the resultant is neutralized with an acid, and a reduction treatment is performed thereto with zinc.

Patent Document 3 discloses a method in which, in a method in which unsaturated carboxylic acid and a hydrogen sulfide compound are reacted, the obtained reaction medium is acidified to produce mercaptocarboxylic acid, hydrogen sulfide other than hydrogen sulfide provided in the neutralization of the unsaturated carboxylic acid is supplied, and the reaction is performed under the pressurization of at least 8 bar. In addition, Patent Document 3 discloses that a hydrogen sulfide compound is obtained by the reaction of $H_2S$ and sodium hydroxide.

Patent Document 4 discloses a method in which β-unsaturated carboxylic acid and hydrogen sulfide are reacted in an aqueous solution in the presence of a basic compound to produce β-mercaptocarboxylic acid, and the above-described reaction is performed under pressure conditions of 3.5 MPaG to 20.0 MPaG.

Patent Document 5 discloses a method in which when unsaturated nitrile is added to an aqueous solution of alkali hydrosulfide to react, the resultant is neutralized, and is hydrolyzed to prepare mercaptocarboxylic acid, sulfur is used.

Patent Document 6 discloses a method in which after alkali hydroxide is added to thiodipropionic acid to make an alkali salt, the resultant is mixed with an aqueous alkali sulfide solution, and acidification is performed to prepare β-mercaptopropionic acid.

RELATED DOCUMENT

Patent Document

[Patent Document 1] Japanese Unexamined Patent Publication No. S59-29655
[Patent Document 2] Japanese Unexamined Patent Publication No. 2001-187778
[Patent Document 3] PCT Japanese Translation Patent Publication No. 2000-501723
[Patent Document 4] Pamphlet of International Publication No. WO2010/095745
[Patent Document 5] Japanese Unexamined Patent Publication No. H2-121962
[Patent Document 6] Japanese Unexamined Patent Publication No. H4-009363

DISCLOSURE OF THE INVENTION

The techniques of the patent documents described above have the following problems.

In the reaction in Patent document 2, an alkali hydrosulfide is used as a raw material. However, since thiodicarboxylic acid is largely produced as a by-product, the reaction yield was decreased. In addition, it is possible to obtain β-mercaptocarboxylic acid by reduction of the dithiodicarboxylic acid. However, since the used amount of a reducing agent becomes large, manufacturing cost is increased, and there was a problem in that waste is increased after the reaction. On the other hand, the production amount of thiodicarboxylic acid which is a by-product is decreased by increasing the amount of alkali hydroxide. However, the amount of acid used in neutralization becomes large, manufacturing cost is increased, and there was a problem in that waste is increased after the reaction. Moreover, as described in paragraph [0007], the method in the documents is characterized in that hydrosulfide is not used.

In the patent document 3 or 4, the reaction is performed under the pressurization, dithiodicarboxylic acid is largely produced as a by-product in these methods also, and the yield is decreased in the reaction.

In this manner, in the methods disclosed in the related documents, thiodicarboxylic acid is produced as a by-product, yield of β-mercaptocarboxylic acid which is a target compound is low, a method for further increasing the yield is complex, and manufacturing cost is increased.

The present invention has been made to solve the above-described problems, and can be described as follows.

[1] A process for preparing β-mercaptocarboxylic acid comprising:

Step a for reacting a compound represented by a formula: $X^1{}_2S$ ($X^1$ represents hydrogen, Na or K) or a compound represented by a formula: $X^2SH$ ($X^2$ represents Na or K), alkali hydroxide represented by a formula: $X^3OH$ ($X^3$ represents Na or K), and unsaturated carboxylic acid represented by the following General Formula (1) to obtain a reaction solution including a compound represented by the following General Formula (2) and a compound represented by the following General Formula (3), Step b for neutralizing the reaction solution obtained in Step a with an acid to obtain a reaction solution including β-mercaptocarboxylic acid represented by the following General Formula (4) and a compound represented by the following General Formula (5), Step c for distillation-refining the reaction solution obtained in Step b to obtain the β-mercaptocarboxylic acid represented by General Formula (4), and Step d for returning a distillation residue including the compound represented by General Formula (5) in Step c to Step a.

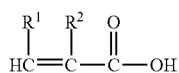

(1)

(In Formula (1), each of $R^1$ and $R^2$ represents hydrogen or a C1 to C4 alkyl group, and may be the same as or different from each other.)

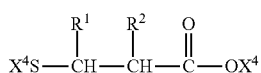

(2)

(In Formula (2), $R^1$ and $R^2$ have the same definition as in Formula (1), $X^4$ represents Na or K. $X^4$ of which two are present may be the same as or different from each other.)

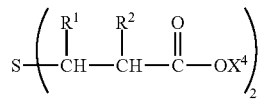

(3)

(In Formula (3), $R^1$ and $R^2$ have the same definition as in Formula (1), $X^4$ represents Na or K. $R^1$, $R^2$ or $X^4$ of which two are present respectively may be the same as or different from each other.)

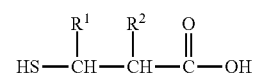

(4)

(In Formula (4), $R^1$ and $R^2$ have the same definition as in Formula (1).)

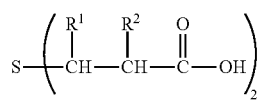

(5)

(In Formula (5), $R^1$ and $R^2$ have the same definition as in Formula (1). $R^1$ and $R^2$ of which two are present respectively may be the same as or different from each other.)

[2] The process for preparing β-mercaptocarboxylic acid described in [1], in which Steps a to d are repeatedly performed.

[3] The process for preparing β-mercaptocarboxylic acid described in [1] or [2], in which the compound represented by the formula: $X^2SH$ is NaSH.

[4] The process for preparing β-mercaptocarboxylic acid described in [1] or [2], in which the compound represented by the formula: $X^1_2S$ is $H_2S$.

[5] The process for preparing β-mercaptocarboxylic acid described in any one of [1] to [4], in which Step a is performed in the presence of sulfur.

According to the present invention, it is possible to obtain β-mercaptocarboxylic acid with high yield. In other words, the present invention can provide a simple method in which β-mercaptocarboxylic acid can be obtained with high yield.

DESCRIPTION OF EMBODIMENTS

Hereinafter, the invention will be described.

The process for preparing β-mercaptocarboxylic acid of the present invention has the following Steps a to d. Each step will be described in order.

[Step a]

A reaction solution including a compound represented by the following General Formula (2) and a compound represented by the following General Formula (3) is obtained by reaction of a compound represented by a formula: $X^1_2S$ ($X^1$ represents hydrogen, Na or K) or a compound represented by a formula: $X^2SH$ ($X^2$ represents Na or K), alkali hydroxide represented by a formula: $X^3OH$ ($X^3$ represents Na or K), and unsaturated carboxylic acid represented by the following General Formula (1).

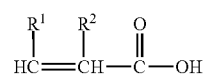

(1)

In Formula (1), each of $R^1$ and $R^2$ represents hydrogen or a C1 to C4 alkyl group, and may be the same as or different from each other.

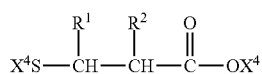

(2)

In Formula (2), $R^1$ and $R^2$ have the same definition as in Formula (1), $X^4$ represents Na or K. $X^4$ of which two are present may be the same as or different from each other.

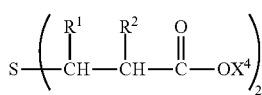

(3)

In Formula (3), $R^1$ and $R^2$ have the same definition as in Formula (1), $X^4$ represents Na or K. $R^1$, $R^2$ or $X^4$ of which two are present respectively may be the same as or different from each other.

Moreover, in the compound represented by General Formulas (2) or (3), $X^4$ is derived from $X^1$, $X^2$ or $X^3$.

As the compounds represented by the formula: $X^1_2S$, $H_2S$, $Na_2S$ and $K_2S$ can be exemplified. As the compounds represented by the formula: $X^2SH$, NaSH and KSH can be exemplified.

In Step a, as the unsaturated carboxylic acid of General Formula (1) in which preferably, each of $R^1$ and $R^2$ independently represents hydrogen or a methyl group, specifically, acrylic acid, methacrylic acid and crotonic acid can be exemplified. In the case where β-mercaptocarboxylic acid used in a plastic lens monomer is prepared, acrylic acid can be used.

Alkali hydroxide is represented by a formula: $X^3OH$ ($X^3$ represents Na or K), and $X^3$ is preferably sodium. Alkali hydroxide is used as an aqueous solution as described in the above-described method. Alkali hydroxide may be dissolved in a mixed solvent of water and alcohol, and alcohol may be separately added thereto. Since a solvent recovery step is not needed, the above method is advantageous from the viewpoint of productivity improvement compared to methods using an organic solvent in the related art.

In the case where $H_2S$ is used, Step a can be performed as follows.

(1) Unsaturated carboxylic acid represented by General Formula (1) is added to an aqueous solution of alkali hydroxide to produce a salt is formed. Next, hydrogen sulfide is blown to react with unsaturated carboxylic acid salt.

(2) Hydrogen sulfide is blown into an aqueous solution of alkali hydroxide, and then, unsaturated carboxylic acid represented by General Formula (1) is added thereto, whereby reaction occurs.

Moreover, in the methods (1) and (2), the example in which unsaturated carboxylic acid is added is described. However, alkali salt of unsaturated carboxylic acid which is prepared in advance using an alkali hydroxide may be used. In this case, Step a can be performed by a method (3) described below.

(3) Hydrogen sulfide is blown into an aqueous solution of alkali hydroxide, and then, aqueous solution containing alkali salt of unsaturated carboxylic acid which is separately prepared by adding unsaturated carboxylic acid to the aqueous solution of alkali hydroxide is added thereto, whereby reaction occurs.

Moreover, the methods described in the (1) to (3) may be performed under atmospheric pressure, or under the pressurization.

As hydrogen sulfide, hydrogen sulfide which is derived from petroleum refining, and hydrogen sulfide which is synthesized by hydrogenation of sulfur can be exemplified. In Step a, in the case where hydrogen sulfide is supplied to an aqueous solution of alkali hydroxide, hydrogen sulfide gas is used. However, liquefied hydrogen sulfide is usually used since storage stability thereof is excellent.

The added amount of hydrogen sulfide is preferably equal to or greater than 1.0 equivalent, and more preferably equal to or greater than 1.5 equivalent with respect to the unsaturated carboxylic acid. The upper limit value is equal to or less than 9.0 equivalent, preferably equal to or less than 5.0 equivalent, and more preferably equal to or less than 3.0 equivalent. These upper limit value and lower limit value can be arbitrarily combined.

A hydrogen sulfide gas can be supplied to the aqueous solution of alkali hydroxide while a temperature of the aqueous solution is maintained at the range of 0° C. to 50° C. Thus, solubility of hydrogen sulfide gas is improved, and the reaction rapidly proceeds. After hydrogen sulfide gas is supplied, the reaction is usually performed in the temperature range of 20° C. to 150° C., preferably in the temperature range of 50° C. to 140° C., and more preferably in the temperature range of 80° C. to 130° C. The temperature range is preferable from the viewpoint of a reaction rate and of reducing the production amount of by-products (dithiodicarboxylic acid and thiodicarboxylic acid). The reaction time can be suitably selected depending on the reaction temperature. The reaction time is usually in the range of 0.5 hours to 20 hours, preferably in the range of 1 hour to 15 hours, more preferably in the range of 2 hours to 10 hours, and still more preferably in the range of 3 hours to 10 hours.

On the other hand, in Step a, in the case where $Na_2S$, $K_2S$, NaSH or KSH are used, an addition order is not particularly limited, and at least one compound selected from these compounds, NaOH, and unsaturated carboxylic acid are mixed to react, the reaction can be also performed under the pressurization.

In Step a, in the case where $Na_2S$, $K_2S$, NaSH or KSH are used, the used amount of these is preferably equal to or greater than 1.0 equivalent, and more preferably equal to or greater than 1.5 equivalent with respect to the unsaturated carboxylic acid. The upper limit value is equal to or less than 9.0 equivalent, preferably equal to or less than 5.0 equivalent, and more preferably equal to or less than 3.0 equivalent. These upper limit values and lower limit values can be arbitrarily combined.

The used amount of alkali hydroxide is in the range of 1 equivalent to 10 equivalents, and preferably in the range of 2 equivalent to 5 equivalent with respect to the unsaturated carboxylic acid.

An addition order of at least one compound selected from $Na_2S$, $K_2S$, NaSH or KSH, alkali hydroxide and unsaturated carboxylic acid is not particularly limited. A temperature range in the addition is preferably in the range of 0° C. to 50° C.

After the addition, usually, the reaction is performed in the temperature range of 20° C. to 150° C., preferably in the temperature range of 50° C. to 140° C., and more preferably in the temperature range of 80° C. to 130° C. The temperature range is preferable from the viewpoint of a reaction rate and of reducing the production amount of by-products (dithiodicarboxylic acid and thiodicarboxylic acid). The reaction time can be suitably selected depending on the reaction temperature. The reaction time is usually in the range of 0.5 hours to 20 hours, preferably in the range of 1 hour to 15 hours, more preferably in the range of 2 hours to 10 hours, and still more preferably in the range of 3 hours to 10 hours.

As the compound represented by a formula: $X^1_2S$, $H_2S$ is preferable from the viewpoint of suppressing the production amount of dithiodicarboxylic acid, and as the compound represented by a formula: $X^2SH$, NaSH is preferable from the viewpoint of the difficulty in handling ability of $H_2S$ gas.

In addition, in Step a, the reaction can be performed in the presence of sulfur in order to promote the reaction. Thus, it is possible to obtain β-mercaptocarboxylic acid with higher yield.

The added amount of sulfur is in the range of 0.01 mol % to 10 mol %, preferably in the range of 0.1 mol % to 5 mol %, and more preferably in the range of 0.1 mol % to 3 mol % with respect to the unsaturated carboxylic acid from the viewpoint of the above-described effect. The addition method is not particularly limited, and at the time of adding unsaturated carboxylic acid or alkali salt of unsaturated carboxylic acid, these are preferably present in aqueous solution.

By Step a, a reaction solution which includes the compound represented by General Formula (2) and the compound represented by General Formula (3) is obtained.

[Step b]

The reaction solution obtained in Step a is neutralized with an acid to obtain a reaction solution including β-mercaptocarboxylic acid represented by the following General Formula (4) and a compound represented by the following General Formula (5).

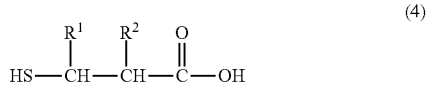

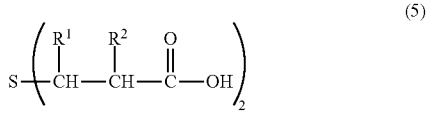

In Formulas (4) and (5), $R^1$ and $R^2$ have the same definition as in Formula (1). In Formula (5), $R^1$ and $R^2$ of which two are present respectively may be the same as or different from each other.

As the acids, inorganic acids such as sulfuric acid, hydrochloric acid, nitric acid and phosphoric acid, and lower carboxylic acids such as formic acid, and acetic acid can be used.

The acid is used in an amount that the reaction system exhibits acidity, and usually, the range of 0.8 equivalents to 1.2 equivalents is suitable with respect to alkali hydroxide which is used in the reaction. At the time of adding, it is preferably performed while checking a pH of the reaction solution with a pH meter.

By Step b, a reaction solution including β-mercaptocarboxylic acid represented by General Formula (3) and thiodicarboxylic acid can be obtained. In addition to these compounds, dithiodicarboxylic acid which is produced from β-mercaptocarboxylic acid is included in the reaction solution.

[Reduction Step]

In the present invention, a step in which produced dithiodicarboxylic acid is reduced by a metal is included from the viewpoint of improving the yield of β-mercaptocarboxylic acid. Moreover, the reduction step can be performed after Step b (neutralizing step) or simultaneously with Step b.

In the reducing step, β-mercaptocarboxylic acid which is a target substance is not immediately obtained from the reaction mixture after neutralization. A reducing agent is added to the solution after the reaction is completed, or the reaction solution obtained by the neutralization, and a reduction reaction is performed under acidic conditions. Thus, dithiodicarboxylic acid which is a by-product can be converted to β-mercaptocarboxylic acid, and the improvement of the yield can be achieved.

A metal which is a reducing agent includes zinc, iron and tin and the like. Among these, iron is preferably used from the viewpoint of economic efficiency and reduction of the burden on the environment. Moreover, these reducing agents may used singly or in a combination of two or more kinds thereof. The used amount of the reducing agent is preferably in the range of 0.4 mole to 5 moles, and more preferably in the range of 0.5 moles to 3 moles with respect to 1 mole of dithiodicarboxylic acid which is obtained as a by-product from the viewpoint of improving the yield and economic efficiency.

[Step c]

In Step c, the reaction solution obtained in Step b is purified by distillation, and β-mercaptocarboxylic acid represented by General Formula (4) is obtained.

Since mercaptocarboxylic acid is dissolved in an aqueous layer obtained after neutralization of the reaction solution obtained in Step b, it is extracted from the aqueous layer by an organic solvent. As the organic solvents, ethyl acetate, butyl acetate, chloroform, dichloromethane, diethyl ether, isopropyl ether, methyl ethyl ketone and isobutyl ketone can be used, and ethyl acetate and butyl acetate are preferably used.

After the extraction, the organic solvents are removed by concentration under reduced pressure or atmospheric pressure, and mercaptocarboxylic acid which is a target substance can be obtained by performing a distillation refinement. Moreover, the aqueous solution obtained after the extraction is an aqueous solution of inorganic salts such as high concentration sodium sulfate or sodium chloride, and for example, an aqueous solution of high purity sodium sulfate can be used. In addition, if crystals are precipitated from high concentration sodium sulfate solution, the precipitated crystals can be used as extremely high purity sodium sulfate. Furthermore, since organic substance and nitrogen compounds are rarely contained in the waste liquid, there is no the influence on the environment, pollution treatment is also very simple and economical.

In the case of being purified by distillation, distillation apparatus used for distillation is not particularly limited, and known distillation apparatus such as a batch type distillation apparatus, a continuous distillation apparatus and a tower type distillation apparatus can be used. In the case where industrially distilling a large amount, the continuous distillation apparatus composed of a heater, a rectifier and a condenser is preferably used from the viewpoint of stabilization of quality and productivity improvement.

[Step d]

A distillation residue including a compound (thiodicarboxylic acid) represented by General Formula (5) in Step c is returned to Step a.

Thiodicarboxylic acid which is included in the distillation residue can be used as a raw material of β-mercaptocarboxylic acid. At this time, from the viewpoint of liquid-transfer of the distillation residue, after the temperature was increased to give fluidity thereto, or the distillation residue was diluted with a solvent, the distillation residue was returned to the reaction step, and it can be provided to the reaction. In addition, in the distillation step, without distilling off the total amount of the β-mercaptocarboxylic acid, distillation ending at a state in which β-mercaptocarboxylic acid was in the range of 5% to 50%, and preferably in the range of 10% to 30% in the distillation residue, it was returned to the reaction step as β-mercaptocarboxylic acid solution of thiodicarboxylic acid, and it can also be provided to the reaction.

In the present embodiment, Steps a to d can be repeatedly performed.

Moreover, since the compound represented by General Formula (5) is separately supplied in Step a in which a next reaction is performed after Step d (recycling step), it is necessary to appropriately change the amount of the raw material depending on the supply amount.

In the case where the distillation residue is returned to Step a, and the next reaction is performed, it is preferable that the amount of the raw material be appropriately changed from the viewpoint of constantly maintaining a yield per each batch.

From the above-described viewpoint, specifically, it is possible to adjust the amount of unsaturated carboxylic acid used in Step a, and the amount of the compound represented by a formula: $X^1_2S$ ($X^1$ represent hydrogen, Na or K), the amount of the compound represented by a formula: $X^2SH$ ($X^2$ represent Na or K), or the amount of alkali hydroxide represented by a formula: $X^3OH$ ($X^3$ represent Na or K) which are other raw materials used in Step a based on the amount of β-mercaptocarboxylic acid and thiodicarboxylic acid contained in the distillation residue.

By repeatedly performing the step, a final yield of β-mercaptocarboxylic acid can be improved.

The present invention has been described above, and other configuration can be also employed within a range not interfering with the effect of the present invention.

EXAMPLE

Hereinafter, the present invention will be further described in more detail with the examples, and the scope of the present invention is not limited to the examples.

Example 1

In Example 1, Reactions 1 to 6 are sequentially performed. Hereinafter, the reactions will be sequentially described.

(Reaction 1)

A 5-necked flask provided with a stirring apparatus, a thermometer, a cooling tube, a dropping funnel and a blowing tube was prepared, 36.3 g (0.88 mol) of 97% sodium hydroxide and 43.3 g of water were introduced thereto, and the resultant was stirred until it became uniform. While maintaining the inner temperature of the flask at the range of 45° C. to 50° C. by heating the flask in an oil bath, 14.4 g (0.20 mol) of acrylic acid was added dropwise from the dropping funnel over 0.5 hours.

After the dropping ended, 12.6 g (0.37 mol) of hydrosulfide gas was blown into the reaction solution through the flow meter from a liquefied hydrosulfide bombe (manufactured by Sumitomo Seika Chemicals Co., Ltd.) at the same temperature over 88 minutes. After the blowing ended, the temperature was raised to 100° C., and reaction was performed at the same temperature over 8 hours.

After the reaction ended, when quantitative analysis of the reaction solution was performed by a HPLC, 86 mol % of β-mercaptopropionic acid sodium salt, and 13 mol % of thiodipropionic acid sodium salt and 0.4 mol % of dithiodipropionic acid sodium salt as a by-product were produced.

After 0.04 g (0.0007 mol) of Fe powder was introduced into the reaction system, while blowing nitrogen gas thereinto, 129.5 g (0.462 mol) of 35% aqueous sulfuric acid was added dropwise over 2.5 hours to neutralize the reaction solution. Hydrosulfide generated at this time was discharged from the upper portion of the cooling tube out of the system. In the composition of reaction mass after neutralization, β-mercaptopropionic acid was 86.2 mol %, thiodipropionic acid which is a by-product was 13 mol %, and dithiodipropionic acid was not detected.

After the degassing ended, 18.0 g of butyl acetate was introduced thereto, and an extraction operation was performed. 18.0 g of butyl acetate was further introduced to the aqueous layer obtained by a separating, and the same extraction operation was performed three times.

After the butyl acetate layers obtained by the extraction of three times were combined into one, butyl acetate was removed using an evaporator. The obtained concentrated liquid was introduced into a kettle of a distillation apparatus with a single pipe, and distillation was performed under vacuum of 1.2 KPa. Distillation ended when the kettle temperature was increased up to 150° C. As the main fraction, 17.5 g (0.165 mol) of β-mercaptopropionic acid having a purity of 99.9% was obtained. The yield was 82.5% with respect to acrylic acid.

The distillation residue (A) of 2.9 g had fluidity even at 90° C., and in the composition, β-mercaptopropionic acid was 15.5% by weight (0.004 mol %), and thiodipropionic acid was 80.0% by weight (0.013 mol %).

(Reaction 2)

An aqueous solution in which 36.3 g (0.88 mol) of 97% sodium hydroxide and 43.3 g of water were uniformly dissolved was prepared in a 5-necked flask provided with a stirring apparatus, a thermometer, a cooling tube, a dropping funnel and a blowing tube, and the distillation residue (A) obtained in Reaction 1 in a state with fluidity while keeping the temperature at the range of 90° C. to 95° C. was slowly added to the aqueous solution. While maintaining the inner temperature at the range of 45° C. to 50° C., 12.2 g (0.17 mol) of acrylic acid was added dropwise from the dropping funnel over 0.5 hours.

After the dropping ended, 12.6 g (0.37 mol) of hydrosulfide gas was blown into the reaction solution at the same temperature over 90 minutes through the flow meter from a liquefied hydrosulfide bombe (manufactured by Sumitomo Seika Chemicals Co., Ltd.). After the blowing ended, the temperature was raised to 100° C., and reaction was performed at the same temperature over 8 hours.

After the reaction ended, when quantitative analysis of the reaction solution was performed by a HPLC, 0.172 mol of β-mercaptopropionic acid sodium salt, and 0.013 mol of thiodipropionic acid sodium salt and 0.0004 mol of dithiodipropionic acid sodium salt as a by-product were produced.

Neutralization, extraction and distillation operation were performed in the same operation as Reaction 1, and 17.5 g (0.165 mol) of β-mercaptopropionic acid having a purity of 99.9% was obtained as a main fraction. A cumulative yield of β-mercaptopropionic acid (0.165 mol+0.165 mol) obtained in Reactions 1 and 2 was 89.2% with respect to acrylic acid (0.20 mol+0.17 mol) used in Reactions 1 and 2 (one recycling).

The distillation residue (B) of 3.0 g had fluidity even at 90° C., and in the composition, β-mercaptopropionic acid was 14.9% by weight (0.004 mol), and thiodipropionic acid was 79.3% by weight (0.013 mol).

(Reactions 3 to 6)

Hereinafter, in the same manner as Reaction 2, the distillation residue obtained by distillation is returned to reaction step of the next reaction to perform a reaction, and reactions 3 to 6 (four recycling) were performed.

In the above manner, recycling was performed a total of five times. The used amount of the raw materials in Reactions 1 to 6 and the cumulative yield of β-mercaptopropionic acid are shown in Table 1.

TABLE 1

| | Reaction | | | | Reaction product | | Composition of distillation residue | | | |
|---|---|---|---|---|---|---|---|---|---|---|
| | | | | | β-mercaptopropionic acid | | | | | |
| Reaction No. | NaOH (mol) | Acrylic acid (mol) | $H_2S$ (mol) | Distillation residue No. | Production amount (mol) | Cumulative yield* (%) | No | β-mercaptopropionic acid (mol) | Thiodipropionic acid (mol) | Dithiodipropionic acid (mol) |
| 1 | 0.88 | 0.200 | 0.37 | — | 0.165 | 82.5 | A | 0.004 | 0.013 | 0 |
| 2 | 0.88 | 0.170 | 0.37 | A | 0.165 | 89.2 | B | 0.004 | 0.013 | 0 |
| 3 | 0.88 | 0.170 | 0.37 | B | 0.165 | 91.7 | C | 0.004 | 0.013 | 0 |
| 4 | 0.88 | 0.170 | 0.37 | C | 0.165 | 93.0 | D | 0.004 | 0.013 | 0 |
| 5 | 0.88 | 0.170 | 0.37 | D | 0.165 | 93.8 | E | 0.004 | 0.013 | 0 |
| 6 | 0.88 | 0.170 | 0.37 | E | 0.165 | 94.4 | F | 0.004 | 0.013 | 0 |

*(Cumulative production amount (mol) of β-mercaptopropionic acid/cumulative used amount (mol) of acrylic acid) × 100

Example 2

In Example 2, Reactions 1 to 6 are sequentially performed. Hereinafter, the reactions will be sequentially described.

(Reaction 1)

A 5-necked flask provided with a stirring apparatus, a thermometer, a cooling tube, a dropping funnel and a blowing tube was prepared, 36.3 g (0.88 mol) of 97% sodium hydroxide and 43.3 g of water and 0.072 g (0.0022 mol) of sulfur were introduced thereto, and the resultant was stirred until it became uniform. While maintaining the inner temperature of the flask at the range of 45° C. to 50° C. by heating the flask in an oil bath, 14.4 g (0.20 mol) of acrylic acid was added dropwise from the dropping funnel over 0.5 hours.

After the dropping ended, 12.6 g (0.37 mol) of hydrosulfide gas was blown into the reaction solution at the same temperature over 88 minutes through the flow meter from a liquefied hydrosulfide bombe (manufactured by Sumitomo Seika Chemicals Co., Ltd.). After the blowing ended, the temperature was raised to 100° C., and reaction was initiated. When the reaction was conducted while performing a lap analysis of the reaction mass, 84.0 mol % of β-mercaptopropionic acid sodium salt, and 14.9 mol % of thiodipropionic acid sodium salt, and 0.5 mol % of dithiodipropionic acid sodium salt as a by-product were produced 2 hours after the reaction was initiated.

When the reaction ended 5 hours after the reaction was initiated, 86.9 mol % of β-mercaptopropionic acid sodium salt, and 11.8 mol % of thiodipropionic acid sodium salt and 0.8 mol % of dithiodipropionic acid sodium salt as a by-product were produced.

After 0.08 g (0.0014 mol) of Fe powder was introduced into the reaction system, while blowing nitrogen gas thereinto, 129.5 g (0.462 mol) of 35% aqueous sulfuric acid was added dropwise over 2.5 hours to neutralize the reaction solution. Hydrosulfide generated at this time was discharged from the upper portion of the cooling tube out of the system. In the composition of reaction mass after neutralization, β-mercaptopropionic acid was 87.7 mol %, thiodipropionic acid which is a by-product was 11.8 mol %, and dithiodipropionic acid was not detected.

After the degassing ended, 18.0 g of butyl acetate was introduced thereto, and an extraction operation was performed. 18.0 g of butyl acetate was further introduced to the aqueous layer obtained by a separating, and the same extraction operation was performed three times.

After the butyl acetate layers obtained by the extraction of three times were combined into one, butyl acetate was removed using an evaporator. The obtained concentrated liquid was introduced into a kettle of a distillation apparatus with a single pipe, and distillation was performed under vacuum of 1.2 KPa. Distillation ended when the kettle temperature was increased up to 150° C. As the main fraction, 17.8 g (0.168 mol) of β-mercaptopropionic acid having a purity of 99.9% was obtained. The yield was 83.8% with respect to acrylic acid.

The distillation residue (A) of 2.7 g had fluidity even at 90° C., and in the composition, β-mercaptopropionic acid was 16.9% by weight (0.004 mol), and thiodipropionic acid was 78.9% by weight (0.012 mol %).

(Reaction 2)

An aqueous solution in which 36.3 g (0.88 mol) of 97% sodium hydroxide and 43.3 g of water, and 0.072 g (0.0022 mol) of sulfur were uniformly dissolved was prepared in a 5-necked flask provided with a stirring apparatus, a thermometer, a cooling tube, a dropping funnel and a blowing tube. The distillation residue (A) obtained in Reaction 1 in a state with fluidity while keeping the temperature at the range of 90° C. to 95° C. was slowly added to the aqueous solution. While maintaining the inner temperature at the range of 45° C. to 50° C., 12.4 g (0.172 mol) of acrylic acid was added dropwise from the dropping funnel over 0.5 hours.

After the dropping ended, 12.6 g (0.37 mol) of hydrosulfide gas was blown into the reaction solution at the same temperature over 90 minutes through the flow meter from a liquefied hydrosulfide bombe (manufactured by Sumitomo Seika Chemicals Co., Ltd.). After the blowing ended, the temperature was raised to 100° C., and reaction was performed at the same temperature over 5 hours.

After the reaction ended, when quantitative analysis of the reaction solution was performed by a HPLC, 0.174 mol of β-mercaptopropionic acid sodium salt, and 0.012 mol of thiodipropionic acid sodium salt and 0.0016 mol of dithiodipropionic acid sodium salt as a by-product were produced.

Neutralization, extraction and distillation operation were performed in the same manner as Reaction 1, and 17.8 g (0.168 mol) of β-mercaptopropionic acid having a purity of 99.9% was obtained as a main fraction. A cumulative yield of β-mercaptopropionic acid (0.165 mol+0.165 mol) obtained in Reactions 1 and 2 was 90.3% with respect to acrylic acid (14.4 g+12.4 g) used in Reactions 1 and 2 (one recycling).

The distillation residue (B) of 2.8 g had fluidity even at 90° C., and in the composition, β-mercaptopropionic acid was 16.2% by weight (0.004 mol), and thiodipropionic acid was 75.8% by weight (0.012 mol).

(Reactions 3 to 6)

Hereinafter, in the same manner as Reaction 2, the distillation residue obtained by distillation is returned to reaction step of the next reaction to perform a reaction, and Reactions 3 to 6 (four recycling) were performed.

In the above manner, recycling was performed a total of five times. The used amount of the raw materials in Reactions 1 to 6 and the cumulative yield of β-mercaptopropionic acid are shown in Table 2.

TABLE 2

| | Reaction | | | | Reaction product | | Composition of distillation residue | | |
|---|---|---|---|---|---|---|---|---|---|
| | | | | | β-mercaptopropionic acid | | | | |
| Reaction No. | NaOH (mol) | Acrylic acid (mol) | H₂S (mol) | Distillation residue No. | Production amount (mol) | Cumulative yield* (%) | No | β-mercaptopropionic acid (mol) | Thiodipropionic acid (mol) | Dithiodipropionic acid (mol) |
| 1 | 0.88 | 0.200 | 0.37 | — | 0.168 | 83.8 | A | 0.004 | 0.012 | 0 |
| 2 | 0.88 | 0.172 | 0.37 | A | 0.168 | 90.3 | B | 0.004 | 0.012 | 0 |
| 3 | 0.88 | 0.172 | 0.37 | B | 0.168 | 92.6 | C | 0.004 | 0.012 | 0 |
| 4 | 0.88 | 0.172 | 0.37 | C | 0.168 | 93.9 | D | 0.004 | 0.012 | 0 |

TABLE 2-continued

| | | | | | Reaction product | | | | | |
|---|---|---|---|---|---|---|---|---|---|---|
| | Reaction | | | | β-mercaptopropionic acid | | Composition of distillation residue | | | |
| Reaction No. | NaOH (mol) | Acrylic acid (mol) | H₂S (mol) | Distillation residue No. | Production amount (mol) | Cumulative yield* (%) | No | β-mercaptopropionic acid (mol) | Thiodipropionic acid (mol) | Dithiodipropionic acid (mol) |
| 5 | 0.88 | 0.172 | 0.37 | D | 0.168 | 94.6 | E | 0.004 | 0.012 | 0 |
| 6 | 0.88 | 0.172 | 0.37 | E | 0.168 | 95.1 | F | 0.004 | 0.012 | 0 |

*(Cumulative production amount (mol) of β-mercaptopropionic acid/cumulative used amount (mol) of acrylic acid) × 100

Example 3

In Example 3, Reactions 1 to 6 are sequentially performed. Hereinafter, the reactions will be sequentially described.

(Reaction 1)

A 5-necked flask provided with a stirring apparatus, a thermometer, a cooling tube, a dropping funnel and a blowing tube was prepared, 21.0 g (0.51 mol) of 97% sodium hydroxide and 41.6 g of water were introduced thereto, 29.6 g (0.37 mol) of 70% sodium hydrosulfide (manufactured by Wako Pure Chemical Industries, Ltd.) was introduced thereto, and the resultant was stirred until it became uniform.

While maintaining the inner temperature of the flask at the range of 45° C. to 50° C. by heating the flask in an oil bath, 14.4 g (0.20 mol) of acrylic acid was added dropwise from the dropping funnel over about 0.5 hours. After the dropping ended, the temperature was raised to 100° C., and reaction was performed at the same temperature over 8 hours.

After the reaction ended, when analysis of the reaction mass was performed by a HPLC, 87.3 mol % of β-mercaptopropionic acid sodium salt, 12.0 mol % of thiodipropionic acid sodium salt and 0.7 mol % of dithiodipropionic acid sodium salt as a by-product were produced.

After 0.83 g (0.015 mol) of Fe powder was introduced into the reaction system, while blowing nitrogen gas thereinto, 129.5 g (0.462 mol) of 35% aqueous sulfuric acid was added dropwise over 2.5 hours to neutralize the reaction solution. Hydrosulfide generated at this time was discharged from the upper portion of the cooling tube out of the system. In addition, in the composition of reaction mass after neutralization, β-mercaptopropionic acid was 87.6 mol %, and thiodipropionic acid and dithiodipropionic acid which are by-products were 12.0 mol % and 0.4 mol %, respectively.

After the degassing ended, 18.0 g of butyl acetate was introduced thereto, and an extraction operation was performed. 18.0 g of butyl acetate was further introduced to the aqueous layer obtained by a separating, and the same extraction operation was performed three times.

After the butyl acetate layers obtained by the extraction of three times were combined into one, butyl acetate was removed using an evaporator. The obtained concentrated liquid was introduced into a kettle of a distillation apparatus with a single pipe, and distillation was performed under vacuum of 1.2 KPa. Distillation ended when the kettle temperature was increased up to 150° C. The residue in the kettle had fluidity even at 90° C. As the main fraction, 17.8 g (0.167 mol) of β-mercaptopropionic acid having a purity of 99.9% was obtained. The yield was 83.7% with respect to acrylic acid.

The distillation residue (A) was 2.7, and in the composition, β-mercaptopropionic acid was 16.2% by weight (0.004 mol), thiodipropionic acid was 80.5% by weight (0.012 mol), and dithiodipropionic acid was 3.0% by weight (0.0004 mol).

(Reaction 2)

After 21.0 g (0.51 mol) of 97% sodium hydroxide and 41.6 g of water were introduced in a 5-necked flask provided with a stirring apparatus, a thermometer, a cooling tube, a dropping funnel and a blowing tube, 29.6 g (0.37 mol) of 70% sodium hydrosulfide (manufactured by Wako Pure Chemical Industries, Ltd.) was introduced thereto, and the resultant was stirred until it became uniform, thereby preparing a uniformly dissolved aqueous solution. The distillation residue (A) obtained in Reaction 1 in a state with fluidity while keeping the temperature at the range of 90° C. to 95° C. was slowly added to the aqueous solution. While maintaining the inner temperature at the range of 45° C. to 50° C., 12.4 g (0.172 mol) of acrylic acid was added dropwise from the dropping funnel over 0.5 hours.

After the dropping ended, 12.6 g (0.37 mol) of hydrosulfide gas was blown into the reaction solution through the flow meter from a liquefied hydrosulfide bombe (manufactured by Sumitomo Seika Chemicals Co., Ltd.) at the same temperature over 90 minutes. After the blowing ended, the temperature was raised to 100° C., and reaction was performed at the same temperature over 5 hours.

After the reaction ended, when quantitative analysis of the reaction solution was performed by a HPLC, 0.175 mol of β-mercaptopropionic acid sodium salt, and 0.012 mol of thiodipropionic acid sodium salt and 0.0011 mol of dithiodipropionic acid sodium salt as a by-product were produced.

Neutralization, extraction and distillation operation were performed in the same manner as Reaction 1, and 17.8 g (0.168 mol) of β-mercaptopropionic acid having a purity of 99.9% was obtained as a main fraction. A cumulative yield of β-mercaptopropionic acid (0.167 mol+0.168 mol) obtained in Reactions 1 and 2 was 90.1% with respect to acrylic acid (0.200 mol+0.172 mol) used in Reactions 1 and 2 (one recycling).

The distillation residue (B) of 2.7 g had fluidity even at 90° C., and in the composition, β-mercaptopropionic acid was 16.2% by weight (0.004 mol), thiodipropionic acid was 80.5% by weight (0.012 mol), and dithiodipropionic acid was 3.0% by weight (0.0004 mol), (Reactions 3 to 6)

Hereinafter, in the same manner as Reaction 2, the distillation residue obtained by distillation is returned to reaction step of the next reaction to perform a reaction, and Reactions 3 to 6 (four recycling) were performed.

In the above manner, recycling was performed a total of five times. The used amount of the raw materials in Reactions 1 to 6 and the cumulative yield of β-mercaptopropionic acid are shown in Table 3.

TABLE 3

| | | Reaction | | | β-mercaptopropionic acid | | Reaction product | | | |
| --- | --- | --- | --- | --- | --- | --- | --- | --- | --- | --- |
| | | | | | | | | Composition of distillation residue | | |
| Reaction No. | NaOH (mol) | Acrylic acid (mol) | NaSH (mol) | Distillation residue No. | Production amount (mol) | Cumulative yield* (%) | No | β-mercaptopropionic acid (mol) | Thiodipropionic acid (mol) | Dithiodipropionic acid (mol) |
| 1 | 0.51 | 0.200 | 0.37 | — | 0.167 | 83.7 | A | 0.004 | 0.012 | 0.0004 |
| 2 | 0.51 | 0.172 | 0.37 | A | 0.168 | 90.1 | B | 0.004 | 0.012 | 0.0004 |
| 3 | 0.51 | 0.172 | 0.37 | B | 0.168 | 92.5 | C | 0.004 | 0.012 | 0.0004 |
| 4 | 0.51 | 0.172 | 0.37 | C | 0.168 | 93.7 | D | 0.004 | 0.012 | 0.0004 |
| 5 | 0.51 | 0.172 | 0.37 | D | 0.168 | 94.5 | E | 0.004 | 0.012 | 0.0004 |
| 6 | 0.51 | 0.172 | 0.37 | E | 0.168 | 95.1 | F | 0.004 | 0.012 | 0.0004 |

*(Cumulative production amount (mol) of β-mercaptopropionic acid/cumulative used amount (mol) of acrylic acid) × 100

Comparative example 1

A 5-necked flask provided with a stirring apparatus, a thermometer, a cooling tube, a dropping funnel and a blowing tube was prepared, 36.3 g (0.88 mol) of 97% sodium hydroxide and 43.3 g of water were introduced thereto, and the resultant was stirred until it became uniform. While maintaining the inner temperature of the flask at the range of 45° C. to 50° C. by heating the flask in an oil bath, 14.4 g (0.20 mol) of acrylic acid was added dropwise from the dropping funnel over 0.5 hours.

After the dropping ended, 12.6 g (0.37 mol) of hydrosulfide gas was blown into the reaction solution through the flow meter from a liquefied hydrosulfide bombe (manufactured by Sumitomo Seika Chemicals Co., Ltd.) at the same temperature over 88 minutes. After the blowing ended, the temperature was raised to 100° C., and reaction was performed at the same temperature over 8 hours.

After the reaction ended, when quantitative analysis of the reaction solution was performed by a HPLC, 86 mol % of β-mercaptopropionic acid sodium salt, and 13 mol % of thiodipropionic acid sodium salt and 0.4 mol % of dithiodipropionic acid sodium salt as a by-product were produced.

After 0.04 g (0.0007 mol) of Fe powder was introduced into the reaction system, while blowing nitrogen gas thereinto, 129.5 g (0.462 mol) of 35% aqueous sulfuric acid was added dropwise over 2.5 hours to neutralize the reaction solution. Hydrosulfide generated at this time was discharged from the upper portion of the cooling tube out of the system. In the composition of reaction mass after neutralization, β-mercaptopropionic acid was 86.2 mol %, thiodipropionic acid which is a by-product was 13 mol %, and dithiodipropionic acid was not detected.

After the degassing ended, 18.0 g of butyl acetate was introduced thereto, and an extraction operation was performed. 18.0 g of butyl acetate was further introduced to the aqueous layer obtained by a separating, and the same extraction operation was performed three times.

After the butyl acetate layers obtained by the extraction of three times were combined into one, butyl acetate was removed using an evaporator. The obtained concentrated liquid was introduced into a kettle of a distillation apparatus with a single pipe, and distillation was performed under vacuum of 1.2 KPa. Distillation ended when the kettle temperature was increased up to 150° C. As the main fraction, 17.6 g (0.165 mol) of β-mercaptopropionic acid having a purity of 99.9% was obtained. The yield was 82.5% with respect to acrylic acid.

Comparative example 2

A 5-necked flask provided with a stirring apparatus, a thermometer, a cooling tube, a dropping funnel and a blowing tube was prepared, 21.0 g (0.51 mol) of 97% sodium hydroxide and 41.6 g of water were introduced thereto, 29.6 g (0.37 mol) of 70% sodium hydrosulfide (manufactured by Wako Pure Chemical Industries, Ltd.) was further introduced thereto, and the resultant was stirred until it became uniform.

While maintaining the inner temperature of the flask at the range of 45° C. to 50° C. by heating the flask in an oil bath, 14.4 g (0.20 mol) of acrylic acid was added dropwise from the dropping funnel over about 0.5 hours. After the dropping ended, the temperature was raised to 100° C., and reaction was performed at the same temperature over 8 hours.

After the reaction ended, when analysis of the reaction mass was performed by a HPLC, 87.3 mol % of β-mercaptopropionic acid sodium salt, 12.0 mol % of thiodipropionic acid sodium salt and 0.7 mol % of dithiodipropionic acid sodium salt as a by-product were produced.

After 0.83 g (0.015 mol) of Fe powder was introduced into the reaction system, while blowing nitrogen gas thereinto, 129.5 g (0.462 mol) of 35% aqueous sulfuric acid was added dropwise over 2.5 hours to neutralize the reaction solution. Hydrosulfide generated at this time was discharged from the upper portion of the cooling tube out of the system. In addition, in the composition of reaction mass after neutralization, β-mercaptopropionic acid was 87.6 mol %, and thiodipropionic acid and dithiodipropionic acid which are by-products were 12.0 mol % and 0.4 mol %, respectively.

After the degassing ended, 18.0 g of butyl acetate was introduced thereto, and an extraction operation was performed. 18.0 g of butyl acetate was further introduced to the aqueous layer obtained by a separating, and the same extraction operation was performed three times.

After the butyl acetate layers obtained by the extraction of three times were combined into one, butyl acetate was removed using an evaporator. The obtained concentrated liquid was introduced into a kettle of a distillation apparatus with a single pipe, and distillation was performed under vacuum of 1.2 KPa. Distillation ended when the kettle temperature was increased up to 150° C. The residue in the kettle had fluidity even at 100° C. As the main fraction, 17.8 g (0.167 mol) of β-mercaptopropionic acid having a purity of 99.9% was obtained. The yield was 83.7% with respect to acrylic acid.

The present application claims priority based on Japanese Patent Application no. 2011-253455, filed on Nov. 21, 2011, the content of which is incorporated herein by reference.

The invention claimed is:

1. A process for preparing β-mercaptocarboxylic acid comprising:

Step a for reacting a compound represented by a formula: $X^1_2S$ ($X^1$ represents hydrogen, Na or K) or a compound represented by a formula: $X^2SH$ ($X^2$ represents Na or K), alkali hydroxide represented by a formula: $X^3OH$ ($X^3$ represents Na or K), and unsaturated carboxylic acid represented by the following General Formula (1) to obtain a reaction solution comprising a compound represented by the following General Formula (2) and a compound represented by the following General Formula (3);

Step b for neutralizing the reaction solution obtained in Step a with an acid to obtain a reaction solution comprising β-mercaptocarboxylic acid represented by the following General Formula (4) and a compound represented by the following General Formula (5);

Step c for distillation-refining the reaction solution obtained in Step b to obtain the β-mercaptocarboxylic acid represented by General Formula (4) and ending distillation at a state in which β-mercaptocarboxylic acid is contained in the range of 5 wt % to 50 wt % in 100 wt % of a distillation residue; and Step d for returning the distillation residue comprising the compound represented by General Formula (5) in Step c to Step a,

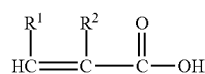
(1)

wherein, in Formula (1), each of $R^1$ and $R^2$ represents hydrogen or a C1 to C4 alkyl group, and may be the same as or different from each other,

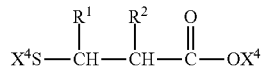
(2)

wherein, in Formula (2), $R^1$ and $R^2$ have the same definition as in Formula (1), $X^4$ represents Na or K, $X^4$ of which two are present may be the same as or different from each other,

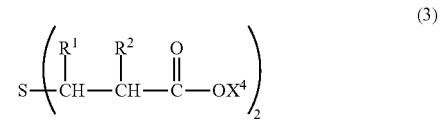
(3)

wherein, in Formula (3), $R^1$ and $R^2$ have the same definition as in Formula (1), $X^4$ represents Na or K, $R^1$, $R^2$ or $X^4$ of which two are present respectively may be the same as or different from each other,

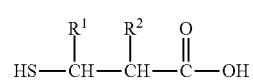
(4)

wherein, in Formula (4), $R^1$ and $R^2$ have the same definition as in Formula (1), and

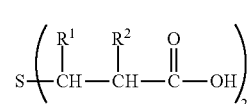
(5)

wherein, in Formula (5), $R^1$ and $R^2$ have the same definition as in Formula (1), $R^1$ and $R^2$ of which two are present respectively may be the same as or different from each other.

2. The process for preparing β-mercaptocarboxylic acid according to claim 1, wherein Steps a to d are repeatedly performed.

3. The process for preparing β-mercaptocarboxylic acid according to claim 1, wherein the compound represented by the formula: $X^2SH$ is NaSH.

4. The process for preparing β-mercaptocarboxylic acid according to claim 1, wherein the compound represented by the formula: $X^1_2S$ is $H_2S$.

5. The process for preparing β-mercaptocarboxylic acid according to claim 1, wherein Step a is performed in the presence of sulfur.

6. The process for preparing β-mercaptocarboxylic acid according to claim 1, wherein the compound represented by the General Formula (5) is a dithiodicarboxylic acid, further comprising Step b1 for reducing the dithiodicarboxylic acid, after Step b.

* * * * *